United States Patent [19]

Arcan et al.

[11] 4,324,547
[45] Apr. 13, 1982

[54] DENTISTRY TECHNIQUE

[75] Inventors: Mircea Arcan, Tel-Aviv, Israel; Benedict Heinrich, Bremen, Fed. Rep. of Germany

[73] Assignee: Vishay Intertechnology, Inc., Malvern, Pa.

[21] Appl. No.: 1,009

[22] Filed: Jan. 4, 1979

[30] Foreign Application Priority Data

Sep. 16, 1978 [DE] Fed. Rep. of Germany ....... 2840365
Sep. 16, 1978 [DE] Fed. Rep. of Germany ... 7827611[U]

[51] Int. Cl.³ .............................................. A61C 9/00
[52] U.S. Cl. ..................................................... 433/71
[58] Field of Search .................. 356/364, 115, 32, 33, 356/34, 35; 433/71, 68; 128/25; 350/149, 153, 157

[56] References Cited

U.S. PATENT DOCUMENTS

| | | | |
|---|---|---|---|
| 3,495,907 | 2/1970 | Rogers | 356/34 |
| 3,604,116 | 8/1970 | Shpuntoff | 433/71 |
| 3,966,326 | 6/1976 | Brull et al. | 356/35 |
| 4,119,380 | 10/1978 | Raftopoulos et al. | 73/800 |

FOREIGN PATENT DOCUMENTS 1253  4/1979  European Pat. Off. ............. 433/71

*Primary Examiner*—Robert Peshock
*Attorney, Agent, or Firm*—Weiser, Stapler & Spivak

[57] ABSTRACT

Qualitative as well as quantitative evaluation of bite characteristics is performed by subjecting to bite forces pieces of material which exhibits photoelastic memory and studying the resulting impression with a polariscope. A permanent record can also be obtained.

58 Claims, 10 Drawing Figures

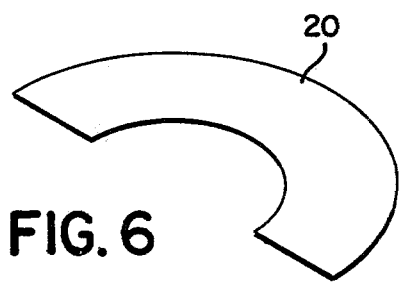
FIG. 6
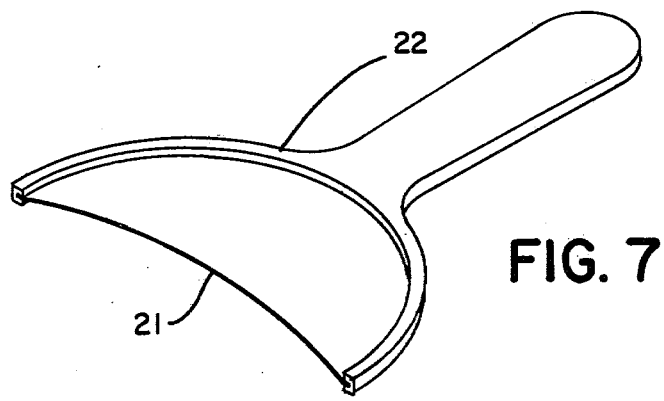
FIG. 7
FIG. 8
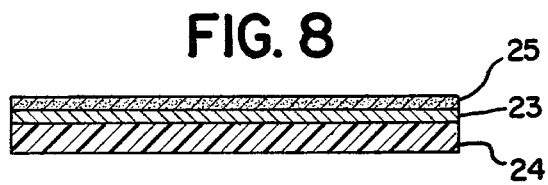
FIG. 9
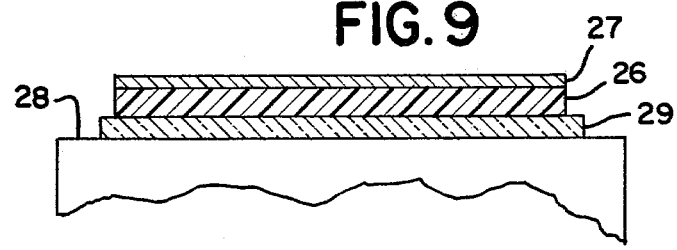

DENTISTRY TECHNIQUE

The invention relates to a method of examining and determining the bite characteristics of sets of teeth, especially human teeth.

The invention relates further to a device for examining and determining the bite characteristics of sets of teeth.

Finally, the invention relates to an instrument for utilizing devices embodying the invention after these have been subjected to biting forces.

Both for medical, and especially dental scientific purposes, as well as in the day-to-day practice of doctors and especially dentists, it is often extremely desirable to ascertain the true characteristics of the bite in order to make correct diagnoses and provide appropriate treatment.

To obtain accurate information about the bite, it is not sufficient to simply x-ray the set of teeth to be examined, which consists essentially of the two opposed jaws with the teeth and/or prostheses enclosed therein. Nor is it enough to take an impression thereof in a mass which starts out plastic and subsequently hardens. These known examination methods indeed provide certain data about the structure and characteristics of the set of teeth. However, they provide only relatively coarse indications concerning the actual occlusion characteristics of opposed teeth or rows of teeth, and no indication at all of the real pressure or contact forces which exist between opposed teeth. Yet, as previously stated, it is extremely important to obtain the most precise information of at least qualitative but preferably also quantitative nature, not only with respect to the occlusion, i.e., the normal closed position of the teeth, but also with respect to the mastication, i.e., the characteristics prevailing during chewing, and also with respect to incision, that is the characteristics which prevail during the cutting phase of biting.

For such gnathologic investigations of teeth arches, there is known a method and apparatus utilizing a piezoelectric transducer which is inserted between the teeth to examined and then subjected to biting pressure. Thereupon the pressure-sensitive transducer produces an electrical signal which can be displayed or recorded by an instrument which has been previously calibrated to register the force applied to the transducer.

However, these known methods and instruments are capable only of measuring the total force applied and give no information about the distribution of the contact forces between the two arches. It is, for example, not possible to mount several such transducers in different locations along an arch and then obtain an effective measurement of the prevailing contact forces. This is because both the piezoelectric transducers and the two arches are comparatively rigid. Therefore a first transducer may absorb the entire mastication force, while a second one remains completely unloaded or loaded only to an insignificant degree.

Moreover, even if the tooth arches were to deform in somewhat elastic manner in response to chewing force application to piezoelectric transducers applied at several points, this would still not provide a reasonably accurate representation of the actual characteristics, either with respect to occlusion, or with respect to mastication, or incisional biting.

It is also apparent that these disadvantages cannot be overcome by reducing the rigidity of such transducers, as for example, by enclosing them within an elastic envelope of rubber or the like. That is because such an arrangement is capable of measuring only localized forces and with relatively great imprecision, whereas it is not possible to ascertain the true bite- or mastication force characteristics at all actual contact points of a set of teeth. Furthermore, this known arrangement is not capable of differentiating between occlusion and mastication, and the results obtained with this known instrumentation also do not provide any indication as to the mechanical-geometric relationships between opposing cusps.

This known instrumentation also does not provide results which take into account the various effects of mouth movement during opening and closing of the arches which accompany food intake and therefore provides no information about the dynamic characteristics.

To obtain at least qualitatively useful data, dental clinics currently use carbon paper, which is placed in strip form between the arches of a set of teeth and which, after biting, provides certain qualitative information about the prevailing contact forces and the mechanical-geometric relationship between the cusps of opposed natural teeth and/or prostheses. This method is relatively practical in that it is simple and quick and thereby suitable for clinical use. However, it does not provide any quantitative data and has only low accuracy even in a qualitative sense.

Methods of examination through impression of arches into plastic materials, such as wax plates or plastic which later hardens, which have previously been briefly mentioned, not only are unable to provide data for contact forces but also are very difficult to interpret with respect to relationships between opposed cusps. Moreover these methods are not capable of providing practical records of observations made.

The present invention has the primary object of improving upon known methods, devices and instruments of the types previously described while overcoming their disadvantages, and to provide a method, devices and instrumentation capable of effecting qualitative and quantitative gnathologic examination and determination of occlusion, mastication and incision over the entire set of teeth. A further desired capability is that of providing differentiating data with respect to occlusion and mastication, and also to provide information concerning the mechanical-geometric relationship between opposed cusps and the dynamic characteristics during mastication. Finally it is desired that the results be not only obtained in simple manner but also capable of being recorded.

To achieve the foregoing objects, there is placed between the teeth to be examined at least one strip-like segment of a material which is not-completely-elastic, optically isotropic, and exhibiting mechanical birefringence. The jaws which hold the teeth to be examined are then pressed together against the strip-like segment. The strip-like segment deformed by the teeth to be examined is removed. Finally the resulting impressions in the strip-like segment are analyzed under polarized light.

Preferably the strip-like segment is kept under pressure between the teeth, or arches to be examined for a predetermined dwell time which may be one minute for example, after bite closure and before removal.

In referring heretofore and hereinafter to a "not-completely-elastic" material, what is meant is a material which is elasto-plastic. Such a material responds to an impression imparted through biting by retaining same as unchanged as possible for at least a predetermined period of time, thereby making possible its analysis and, if desired, its recording.

In referring heretofore or hereinafter to a material which is "optically isotropic, and exhibiting mechanical bire-fringence", what is meant is a material which is initially not birefringent by virtue of being optically isotropic, but which becomes birefringent under stress.

As is well known, birefringence normally occurs only in optically anisotropic media, such as crystals with non-cubic lattices. These split an incident beam into two component beams, which generally have different group orientations and different group and phase velocities, both obeying the conventional laws or refraction. If the media are non-absorbing, then both component beams are polarized linearly and mutually perpendicularly.

However, in addition to the above-described natural birefringence of optically anisotropic crystals, there also exists what is referred to as deformation or stress birefringence, which is produced by external mechanical input or load in normally isotropic media. Such an optically isotropic material subjected to pressure or tension, may then behave like a crystal having a single optical axis, that axis being oriented in the direction of the pressure or tension.

The internal stresses created by loading give rise to the phenomeon which is referred to here as mechanical birefringence. The varying internal stresses can provide an indication for the applied load, provided the material being used has been suitably calibrated.

In order to obtain not only the desired effect of mechanical stress birefringence, but in order to also preserve the phenomena produced by loading for at least a time period sufficient for examination and, if desired, for recording, there is provided in accordance with the invention a material which is not completely elastic. The material in question can therefore be said to exhibit elasto-plastic memory.

Preferably the invention utilizes an elasto-plastic material which is flexible and foil-like. It is particularly preferred to use such a foil of extremely uniform initial thickness.

Particularly suitable materials are polymers, among which polyamids such as nylon or polyethylene are preferred. However other materials can also be used.

If a two-sided impression is desired, then a single strip-like foil segment is preferably used. This yields an impression of one arch on the upper surface of the foil, and an impression of the opposite arch on the lower foil surface. This suffices to enable not only a quantitative determination of the contact forces, but also their correlation with the mechanical-geometric properties of the respective teeth. For example it is possible to discern that the contact force produced at a given opposed pair of teeth is produced by a cusp of the upper tooth engaging a bow-shaped configuration of cusps in the opposed lower tooth, and the like.

On the other hand, if for any reason separate examination of the upper and lower arches is desired, then there are preferably used two such foil segments which are readily separable after the impression has been taken.

In a further embodiment of the invention, a separator is placed between two foil strips. This separator is preferably of elastic or deformable material and has a thickness of 0.5 to 3 mm. This has the further advantage that the presence of the elastic separator layer can simulate the presence of food between the two arches.

Analysis of the segments which have been subjected to biting forces may be performed in accordance with the invention by using an illuminating white or monochromatic light source, a polarizing filter acting as first linear or circular polarizer, a second linear or circular polarizing filter acting as analyzer, a holder for the segments to be analyzed, and magnifying means placed above the illuminating means and polarizing filter. Preferably the holder for the segments is in the form of a scissors clamp, which enables relative tilting.

Another embodiment of the invention, which makes possible the use of reflective optics for stress analysis, involves positioning the illuminating means and first polarizing filter serving as the polarizer on the same (upper) side of the segment to be analyzed as the second polarizing filter and the magnifying means.

Further explanations of the invention are provided below with reference to illustrative embodiments and to the accompanying drawings wherein:

FIG. 6 is a perspective view of a particular shape of a device for examining the bite which embodies the present invention;

FIG. 7 is a perspective view of another shape of such a device and a holder for same;

FIG. 8 is a diagrammatic representation in cross-section of another embodiment of such a device; and FIG. 9 is a diagrammatic representation of a particular manner of utilizing such a device.

Figure 1:
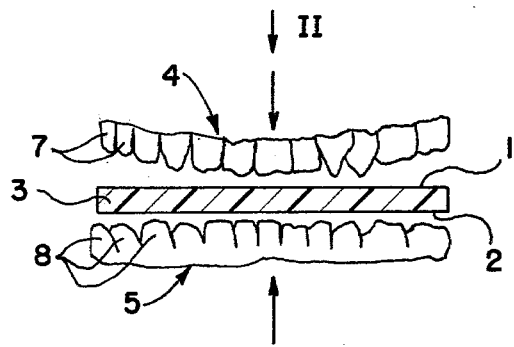
FIG. 1 is a diagrammatic representation in cross-section, of a device for examining and determining the bite characteristics of a set of human teeth, which comprises two parallel foil segments and an elastic separator.

FIG. 1 of the drawings shows a device embodying the invention, in which two strip-like segments 1 and 2 positioned parallel to and spaced from each other, with a separator layer 3 between the two segments 1 and 2. The segments 1 and 2 are of elasto-plastic material and exhibit mechanical birefringence.

The two segments 1 and 2 are of flexible foil having a highly uniform thickness of, for example, 0.15 mm. The foil material may consist of a transparent polyamid, and particularly of nylon.

The separator layer 3 consists of an elastic or deformable material, e.g., rubber and may have a thickness of 1.8 mm, for example.

For gnathologic examination of occlusion, mastication and incision the three-layer structure of FIG. 1 is inserted between the two arches 4 and 5 which are diagrammatically represented in FIG. 1.

The two arches 4 and 5 are then moved toward each other and pressed together.

The device of FIG. 1 remains in its compressed condition between the upper teeth 7 of upper arch 4 and the lower teeth 8 of arch 5 for a period ranging from 10 to 60 seconds. Thereafter the bite is suitably loosened and the device removed from the mouth.

Figure 3A:
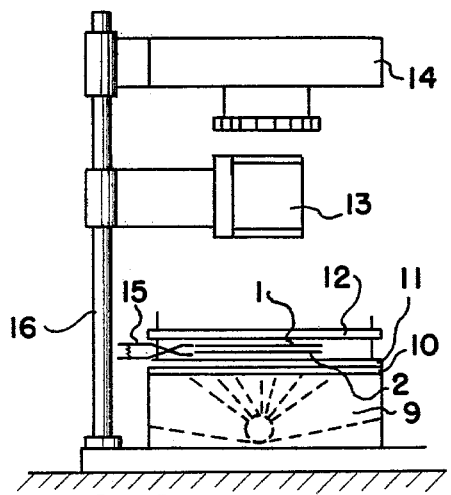
FIG. 3a is a diagrammatic illustration of an instrument for analyzing the results obtained using light transmission.
Figure 3B:
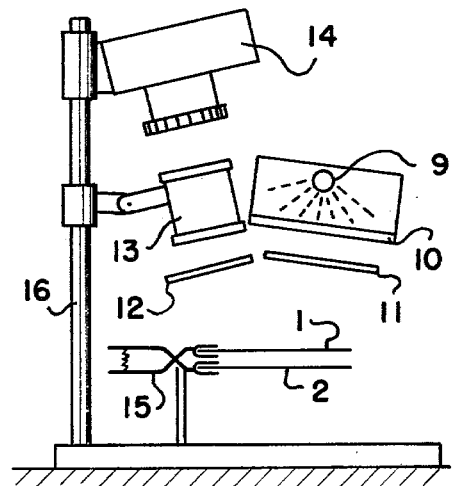
FIG. 3b is a diagrammatic illustration of an instrument for analyzing the results obtained using light reflection.
Figure 5:
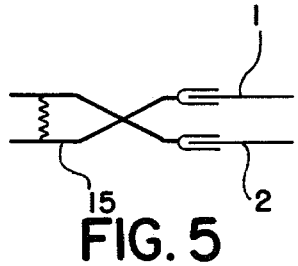
FIG. 5 shows a scissors clamp for holding the segments.

The device or arrangement of FIG. 1 which has been used in that manner is then analyzed by means of the instrumentation of FIGS. 3a or 3b.

The analytical instrument of FIGS. 3a or 3b includes an illuminating means comprising a white light source 9 and a glass diffusion plate 10, two linear or circular polarizing filters 11 and 12, and, for holding the foil segments 1, 2 which are to be analyzed, a holder in the form of scissors clamps 15 which are capable of providing tilting relative to each other Above the upper polarizing filter 12 there is an eyepiece or magnifying lens 13. Normally a 3 to 10-fold magnification by lens 13 is sufficient.

To record the examination results, a camera 14 may be positioned above or in place of eyepiece 13, pivotably attached to stand 16. This makes it possible to either observe or examine the impressions without interference from camera 14, or alternatively to make a recording through photography.

Figure 2:
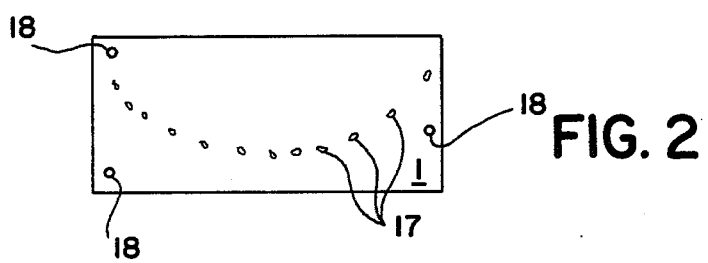
FIG. 2 is a diagrammatic top view of the device of FIG. 1 taken in the direction of arrow II.
Figure 4:
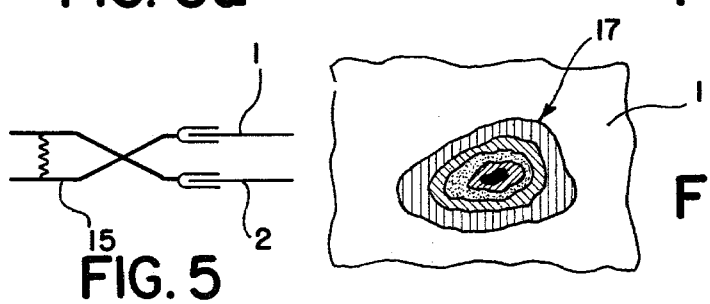
FIG. 4 is a diagrammatic illustration of the enlarged impression of a tooth or cusp observed by means of the instrumentation of FIG. 3.

FIG. 2 shows in highly diagrammatic manner the impressions 17 of upper teeth 7 as they appear as uniform points to the naked eye. On the other hand, FIG. 4 shows, also highly diagrammatically, the appearance to the eye or to the camera in the instrument of either FIG. 3. The irregular areas shown in FIG. 4 with different cross-hatching and dotting, in reality exhibits different colors (isochromatics). Once the material used for foils 1 and 2 has been appropriately calibrated, this makes possible the quantitative determination of the contact forces created by biting.

In addition, these impressions reveal the mechanical-geometric relationships. For example, they make it possible to determine in which locations, and therefore also at which cusps, there occur the contact forces between the teeth under examination.

The impression thus obtainable also reproduces the overall force distribution along the entire arch. In the illustrative embodiment under discussion, the elastic separator layer 3 simulates the conditions which prevail during average food intake.

Corresponding impressions for the teeth 8 of the lower arch 5 exist in segment 2, which can be separated from segment 1 after impression. Using appropriate alignment means, e.g. accurately positioned holes 18, the two segments 1 and 2 may also be superimposed and viewed simultaneously. This provides information about the relationships between confronting cusps.

As will be recognized, the method, devices and instrumentation embodying this invention not only enable determination of the contact forces of normal sets of teeth, but also those which arise when implant supports are used. This therefore provides a remarkable capability for making necessary adjustments, so as to achieve relatively uniform loadings of the implant support, or the like.

The same is obviously true for prosthetic work, so that determination of the prevailing contact forces can avert problems and make possible the achievement of substantial uniformity of forces for occlusion and/or mastication and/or incision.

Furthermore the present invention is also remarkably well suited for the creation of official records, and particularly to supplement fingerprints or other personal identifying indicia. The results obtained by means of the invention do not change over extended periods of time, or at least do not change to such an extent as to preclude identification of a specific person, unless that person has had major prosthetic work performed in the interim.

The phenomena which are employed in the practice of the present invention can be described as follows.

The materials which are suitable for use as segments 1 and 2 have been found to have certain specific characteristics. In particular, when a thin strip of such materials is subjected to localized stress, as is the case if opposed teeth or arches bear down upon it, there results corresponding localized strain. This strain can be visually observed by means such as the instrumentation of FIG. 3, above. It manifests itself through so-called "fringes" surrounding the area under stress. This is sometimes referred to as the photoelastic effect, and the materials exhibiting same are correspondingly referred to as photoelastic materials.

For the purposes of the present invention, there is utilized not only this photoelastic effect, as such, but also a further specific ramification thereof. This stems from the fact that in certain materials, and physical configurations of such materials, the strain which results from applied stress varies more or less proportionately with stress over an initial range of applied stresses, but then ceases to do so when a certain threshold is exceeded. Beyond that threshold, the proportional relationship no longer holds, and the material is not completely relieved of the strains produced therein, even after the stress ceases to be applied. This retention of strain even after removal of the stress may be referred to as "photoelastic memory", or "photomemory" for short. This residual strain attributable to photomemory is what is employed in accordance with the present invention.

The strip-like segments such as segments 1 and 2 previously discussed constitute what may be called photomemory tapes.

When subjected to the bite of a set of teeth as previously explained, the local stresses set up by contact points between opposed teeth give rise to corresponding local strains in the photomemory tape (or tapes if more than one is used).

The type of material and its thickness, as well as other parameters discussed below, are so selected that, under practical bite conditions, that degree of local stress and resulting strain is produced which causes the material to develop corresponding residual photomemory. The time span during which the bite conditions, and therefore pressure, are maintained may range from even as little as two seconds up to one minute, depending on the type and thickness of the material used.

After removal from between the teeth or arches under examination, this residual photomemory is then made visible by means of the instrumentation previously described.

It will be recognized that this instrumentation, per se, is somewhat analogous to known polariscopes, of transmission type for FIG. 3a and of replexion type for FIG. 3b. However, heretofore polariscopes have never been used for examining the bites of teeth, nor have they been used to visualize residual photomemory in photomemory tapes for bite conditions.

Moreover, the construction utilizing scissors clamps 15 has not been used before. This construction makes it possible to take segments 1 and 2, containing the respective photomemory of the bite forces which had acted upon the upper and lower arches, and simultaneously visualize both of them, in the same geometric alignment which prevailed in the actual sets of teeth under examination.

For example, if a cusp in a tooth forming part of one arch fits perfectly within a corresponding fossa of an opposed tooth, then the localized permanent strains set up during biting will be very uniform and give rise to corresponding visible fringe patterns. On the other hand, if there is local misalignment, or some unintended projection on one side or the other, this will set up more intensive, and concentrated local permanent strains in the memory tape, which will manifest themselves as local distortions and intensifications of the fringing effect.

With experience in observing these visual effects, it becomes possible to interpret them quickly and accurately from the stand-point of the corrections to the bite which they indicate to be required. Moreover, by calibrating the memory tapes in advance with known forces, quantitative information concerning the local forces can be derived from the visualization by "counting fringes" and measuring fringe areas. In this respect the procedure is analogous to that conventionally employed with polariscopes.

Moreover, by tilting the tapes 1 and 2 progressively toward or away from each other, there can be observed a visual effect which is strikingly lifelike and representative of the changes which actually take place during movement of the arches toward or away from each other. This is capable of providing valuable clinical insights into the relationships prevailing in the set of teeth under examination.

Preferably, the polarizing filters 11 and 12 are so mounted as to tilt jointly with memory tapes 1 and 2, respectively, said filters being attached for example to the scissors clamps so as to be also displaced by movement of scissors clamps 15.

It is generally desirable to apply, to any surface of a photomemory tape 1 or 2 which is exposed to contact with outside objects, e.g. the teeth to be examined, a protective layer (sheet or coating) of material which does not exhibit the photomemory effect to any substantial degree. This has the purpose of preventing scratches and other unintended deformations from being introduced into the photomemory tape itself. Rather this tape will be "activated" only by the intended bite forces.

If a single tape 1 or 2 is used, then the protective coating is preferably present on both faces of the tape.

If a sandwich of tapes 1 and 2 with separator 3 is used, then the protective coating may be present only on the exposed sides of tapes 1 and 2, respectively.

The material of the protective layer may be Polyvinil cloride and its thickness between 0.01 mm and 1 mm.

The separator layer 3, as previously noted, may be of rubber, or it may be of foam or sponge or potty or wax-like non elastic material. Its thickness preferably ranges from about 0.3 to 3 mm.

It will also be understood that, although the photomemory tapes are preferable isotropic before being subjected to the bite, they may also be initially anisotropic, provided this condition is substantially uniform over the tape. In such a case the pattern when visualized will appear against a generally uniformly colored background.

A photomemory tape in accordance with the present invention may also be provided with a coating or foil of carbon-like material. By so doing, the technique of the present invention may, in effect, be combined with prior known techniques which, as discussed above, use carbon paper to determine certain aspects of bites. In such case, the carbon foil used may serve as the protective layer for the photomemory tape which is mentioned above. If this carbon foil is opaque, it must be stripped off before the photomemory tape is used for visualization. However, a thin coating of carbon-like material can also be applied, which is sufficiently light-transmissive so that no after-treatment is needed before visual utilization, the carbon-like layer can be removed by solvents, water or other liquids. Carbon-like material could be a paint of any color which leaves a trace of color on the teeth when they are brought into contact.

Furthermore, as shown in FIG. 8, a reflective paint layer 23 can be applied to the photomemory tape 24 and a carbon layer 25 on top of the reflective layer 23. Such a device can be analyzed by means of a reflection polariscope without removing the carbon layer 25.

The memory tapes are configured so as to cover the area of the arches to be examined. Preferably, the entire arch is encompassed by the tape. FIG. 6 shows a possible configuration of such a tape 20. FIG. 7 shows another configuration of a tape 21, and also shows that tape 21 inserted in a holder 22 by means of which it can be conveniently inserted and held in place between the arches to be examined. It will be noted that holder 22 is so sized that photomemory tape 21 is slightly bowed. This has been found desirable for good fit between the arches and to provide clearance for the tongue if used in a human mouth.

It is also possible to superimpose on the photomemory tape itself a printed grid of lines for convenient geometric reference of the visual phenomena which will eventually be visualized by its use. It is also possible to superpose other relevant information, such as a dental chart.

It is contemplated that the visualization and analysis of photomemory tapes in accordance with the present invention will normally be performed after removal from between the arches to be examined. However, it is also possible to perform such analysis in situ by opening the arches and using a reflection-type polariscopic instrument. For this purpose, also, there is preferably used a device such as shown in FIG. 8, the reflective layer 23 providing the reflectivity required by the reflection-type polariscopic instrument. The use of a carbon layer 25 is optional insofar as the polariscopic analysis itself is concerned.

To obtain a permanent record of the impressions made in the photomemory tape by the bite, the tape itself may be preserved, and its impression pattern visualized anew, as and when needed, by means of a polariscopic instrument. Alternatively, there may taken a photograph of the visualized pattern, as previously described. The visualized pattern can also be recorded by xerography, as shown in FIG. 9. There a photomemory tape 26 has a reflective coating 27 applied to it. It is then placed upon the bed 28 of a xerographic machine with the tape 26 toward the bed, and with a polarizing filter 29 between tape 26 and bed 28. Filter 29 may be linearly polarizing but is preferably circularly polarized. When tape 26 is illuminated during the initial stage of the xerographic process, the strain pattern therein will become visualized and simultaneously xerographically recorded. Other optical recording techniques may be used in corresponding manner.

The visualized fringe image can also be magnified and projected onto a screen. Then it can be photographed from the screen and also further magnified from the screen by using an eyepiece or microscope. Screens may be used such as movie screens, those of profile projectors, and the like.

We claim:

1. A method of examining and determining the characteristics of a set of teeth and especially of human teeth, comprising
   placing between the teeth to be examined at least one strip-like segment of a material which is not completely elastic (i.e. elasto-plastic), optically isotropic and exhibiting mechanical birefringence (i.e. stress birefringence),
   bringing the jaws which hold the teeth to be examined to bear under pressure against the strip-like segment,
   removing the strip-like segment deformed by the teeth to be examined, and
   studying the impressions formed within the strip-like segment under polarized light.

2. The method of claim 1 wherein
   the strip-like segment remains under load between the teeth for a predetermined period of time.

3. The method of claim 2 wherein
   the period ranges from 10 to 60 seconds.

4. The method of claim 1 wherein
   the material has previously been calibrated with respect to its birefringent properties by application of various loads.

5. The method of claim 1 wherein the material is flexible.

6. The method of claim 5 wherein the material is foil-like.

7. The method of claim 6 wherein the material has highly uniform thickness.

8. The method of claim 7 wherein the thickness is between about 0.1 and 0.3 mm.

9. The method of claim 5 wherein the material is a polymer.

10. The method of claim 9 wherein the polymer is a polyamid such as nylon.

11. The method of claim 9 wherein the polymer is polyethylene.

12. The method of claim 2 wherein the period ranges from about 2 seconds to one minute.

13. The method of claim 1 wherein the segment has a reflective coating on one side, and
    the segment is illuminated from the side opposite the reflective coating.

14. The method of claim 13 wherein the illuminating is through a linearly or circularly polarizing filter.

15. The method of claim 14 wherein the illuminating is by a xerographic reproducing means.

16. The method of claim 14 further comprising making a photographic record of the reflected illumination viewed through the filter.

17. The method of claim 13 wherein the strip-like segment is not removed but is illuminated in situ after the jaws have been opened to permit the illumination to reach the segment.

18. A piece of material for use in examining and evaluating the bite of opposed teeth or sets of teeth, by first placing a piece of material between said teeth or sets of teeth, causing the arches to close upon said material and impress therein a pattern of the bite, and subjecting the resulting patterned material to polariscopic observation, the said piece of material comprising
    at least one layer of a substance of a size and shape to be placed in the mouth between the arches of teeth and which develops under the conditions of the bite residual photomemory that persists after the bite.

19. The piece of claim 18 wherein at least one face of the layer is covered by a protective layer which does not exhibit substantial photomemory under bite conditions.

20. The piece of claim 18 which further comprises a second layer of a substance which exhibits said photomemory.

21. The piece of claim 20 which further comprises a separator layer beween the first and second layers, the separator layer being soft and spongy.

22. The piece of claim 21 wherein the separator layer is selected from the group of rubber, foam, sponge material, putty-like and wax-like material.

23. The piece of claim 21 wherein the exposed faces of both said first and second layers are covered by a protective coating which does not exhibit substantial photomemory under bite conditions.

24. The piece of claim 18 which is of such configuration and dimension as to span the entire set of teeth.

25. The piece of claim 24 which has one edge curved to generally follow the arches of the set of teeth.

26. The piece of claim 25 which is in the general shape of a crescent, having two edges curved to generally follow said arches.

27. The piece of claim 26 which has an edge defining a line connecting the end points of the curve.

28. The piece of claim 27, in combination with holding means configured to hold the piece along the said curved edge.

29. The combination of claim 28 wherein the holding means has a grasping handle extending forward from the curved edge.

30. The combination of claim 28 wherein the holding means is so dimensioned relative to the piece that the piece is bowed out of the plane of the curved edge when held by the holding means.

31. The piece of claim 18 wherein the substance is substantially isotropic before being subjected to the bite conditions.

32. The piece of claim 18 wherein the substance is substantially uniformly anisotropic before being subjected to the bite conditions.

33. The piece of claim 18 wherein at least one face of the layer is covered with a carbon-like coating or transferable paint or foil.

34. The piece of claim 33 wherein the carbon-like cover is a foil and this foil also constitutes a protective coating for said layer.

35. The piece of claim 33 wherein the carbon-like is opaque and susceptible of being stripped off from the layer before the layer is subjected to polariscopic observation.

36. The piece of claim 33 wherein the carbon-like is sufficiently transparent that the layer can be subjected to polariscopic observation, without stripping off the carbon.

37. The piece of claim 33 wherein there is present between the carbon-like and said layer a material which is light reflective at least on the side facing said layer.

38. The piece of carbon-like 37 wherein the light reflective material is an aluminum coating.

39. The piece of claim 18 wherein one face of the layer is covered with a material which is light reflective at least on the side facing said layer.

40. The place of material of claim 18 which has been subjected to the bite conditions, whereby said piece exhibits photomemory of the forces characterizing the conditions of the bite.

41. A permanent record of the photomemory of claim 40 produced by the steps of rendering said photomemory visible in a polariscopic instrument, and additionally recording said visible photomemory.

42. The record of claim 41 wherein the recording is by photography.

43. The record of claim 41 wherein the recording is by xerography.

44. A record of the photomemory of claim 40 produced by the steps of
rendering said photomemory visible in a polariscopic instrument.

45. The record of claim 44 wherein the polariscopic instrument comprises
illuminating means,
a first linear or circular polarizing filter for producing polarization,
a second linear or circular polarizing filter for producing analysis,
means for holding the segments to be analyzed, and,
magnifying means positioned above the illuminating means and polarizing filters.

46. The record of claim 44 wherein the polariscopic instrument comprises
means for holding the piece of material for observation,
the holding means being so constructed that the photomemory impressed into the material by the bite is not substantially disturbed by the holding means.

47. The record of claim 41, the production of which also includes the step of removing the material from the bite conditions before rendering the photomemory visible.

48. The piece of claim 18 wherein the residual photomemory is developed in the form of isochromatics.

49. The piece of claim 18 wherein the material is flexible.

50. The piece of claim 49 wherein the material is foil-like.

51. The piece of claim 50 wherein the material has highly uniform thickness.

52. The piece of claim 51 wherein the thickness is between about 0.1 and 0.3 mm.

53. The piece of claim 18 wherein the material is a polymer.

54. The piece of claim 53 wherein the polymer is a polyamid such as nylon.

55. The piece of claim 53 wherein the polymer is polyethylene.

56. The piece of claim 18 which comprises only a single segment.

57. The piece of claim 21 wherein the separator has a thickness of 0.5 to 3 mm.

58. The piece of claim 18 wherein the layer is of transparent material.

* * * * *